(12) United States Patent
Byrne et al.

(10) Patent No.: US 11,850,396 B2
(45) Date of Patent: Dec. 26, 2023

(54) SYSTEM AND METHOD FOR MONITORING FLUID DEFICIT

(71) Applicant: BOSTON SCIENTIFIC LIMITED, Hamilton (BM)

(72) Inventors: Paul Byrne, Kilkenny (IE); Lee Smith, Waterford (IE); Leah Fanning, Clonmel (IE); Niraj Prasad Rauniyar, Plymouth, MN (US); Nishant Khattar, White Bear Township, MN (US); Vivek Shah, Reading, MA (US); Dipen Arun Tasgaonkar, Clonmel (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 301 days.

(21) Appl. No.: 17/082,769

(22) Filed: Oct. 28, 2020

(65) Prior Publication Data
US 2021/0128815 A1    May 6, 2021

Related U.S. Application Data

(60) Provisional application No. 62/928,005, filed on Oct. 30, 2019.

(51) Int. Cl.
*A61M 5/168* (2006.01)
*A61B 1/015* (2006.01)
(Continued)

(52) U.S. Cl.
CPC .......... *A61M 5/168* (2013.01); *A61B 1/0004* (2022.02); *A61B 1/00097* (2022.02);
(Continued)

(58) Field of Classification Search
None
See application file for complete search history.

(56) References Cited

U.S. PATENT DOCUMENTS

| | | |
|---|---|---|
| 4,655,197 A | 4/1987 | Atkinson |
| 4,902,276 A | 2/1990 | Zakko |

(Continued)

FOREIGN PATENT DOCUMENTS

| | | |
|---|---|---|
| AU | 2018233465 A1 | 8/2019 |
| CA | 2905825 A1 | 10/2014 |

(Continued)

OTHER PUBLICATIONS

International Search Report and Written Opinion dated Feb. 12, 2021 for International Application No. PCT/US2020/057719.

*Primary Examiner* — Dung T Ulsh
(74) *Attorney, Agent, or Firm* — Seager, Tufte & Wickhem, LLP

(57) ABSTRACT

A fluid management and medical device system may include a fluid management system and a medical device having one or more sensors proximate the distal end of the elongate shaft of the medical device. The controller of the fluid management system may be configured to calculate a fluid deficit when the distal end of the elongate shaft is disposed within a patient and configured to automatically pause fluid deficit calculation when the distal end of the elongate shaft is removed from the patient. In some instances the controller is configured to calculate the fluid deficit using rotational speed of the inflow pump in combination with a difference between a change in weight of a fluid supply source supplying fluid to the fluid management system and a change in weight of a collection container collecting fluid from the fluid management system.

16 Claims, 7 Drawing Sheets

(51) Int. Cl.
   *A61B 1/307* (2006.01)
   *A61M 3/02* (2006.01)
   *A61B 1/00* (2006.01)
   *A61M 5/14* (2006.01)

(52) U.S. Cl.
   CPC .............. *A61B 1/015* (2013.01); *A61B 1/307* (2013.01); *A61M 3/0254* (2013.01); *A61M 2005/1402* (2013.01); *A61M 2205/127* (2013.01); *A61M 2205/18* (2013.01); *A61M 2205/3331* (2013.01); *A61M 2205/3334* (2013.01); *A61M 2205/3365* (2013.01); *A61M 2205/3368* (2013.01); *A61M 2205/505* (2013.01); *A61M 2205/52* (2013.01)

(56) References Cited

U.S. PATENT DOCUMENTS

| | | | |
|---|---|---|---|
| 4,994,026 A | 2/1991 | Fecondini | |
| 5,180,896 A | 1/1993 | Gibby et al. | |
| 5,381,510 A | 1/1995 | Ford et al. | |
| 5,403,277 A | 4/1995 | Dodge et al. | |
| 5,437,629 A | 8/1995 | Goldrath | |
| 5,445,610 A | 8/1995 | Evert | |
| 5,460,490 A | 10/1995 | Carr et al. | |
| 5,464,391 A | 11/1995 | DeVale | |
| 5,492,537 A | 2/1996 | Vancaillie et al. | |
| 5,503,626 A | 4/1996 | Goldrath | |
| 5,520,638 A | 5/1996 | O'Quinn et al. | |
| 5,522,805 A | 6/1996 | Vancaillie et al. | |
| 5,571,389 A | 11/1996 | Kerampran | |
| 5,586,973 A | 12/1996 | Emaire et al. | |
| 5,630,798 A | 5/1997 | Beiser et al. | |
| 5,662,611 A | 9/1997 | Beiser et al. | |
| 5,709,670 A | 1/1998 | Vancaillie et al. | |
| 5,733,263 A | 3/1998 | Wheatman | |
| 5,800,383 A | 9/1998 | Chandler et al. | |
| 5,810,770 A | 9/1998 | Chin et al. | |
| 5,875,282 A | 2/1999 | Jordan et al. | |
| 5,919,218 A | 7/1999 | Carr | |
| 5,944,668 A | 8/1999 | Vancaillie et al. | |
| 5,960,160 A | 9/1999 | Clark et al. | |
| 6,024,720 A | 2/2000 | Chandler et al. | |
| 6,046,442 A | 4/2000 | Kawamura et al. | |
| 6,077,246 A | 6/2000 | Kullas et al. | |
| 6,142,974 A | 11/2000 | Kistner et al. | |
| 6,146,359 A | 11/2000 | Carr et al. | |
| 6,159,160 A | 12/2000 | Hsei et al. | |
| 6,186,752 B1 | 2/2001 | Deniega et al. | |
| 6,238,366 B1 | 5/2001 | Savage et al. | |
| 6,261,261 B1 | 7/2001 | Gordon | |
| 6,293,926 B1 | 9/2001 | Sorensen et al. | |
| 6,302,864 B1 | 10/2001 | Nowosielski | |
| 6,319,221 B1 | 11/2001 | Savage et al. | |
| 6,512,212 B1 | 1/2003 | Harris | |
| 6,554,791 B1 | 4/2003 | Cartledge et al. | |
| 6,585,708 B1 | 7/2003 | Maaskamp | |
| 6,746,439 B2 | 6/2004 | Lenker | |
| 6,775,473 B2 | 8/2004 | Augustine et al. | |
| 6,824,528 B1 | 11/2004 | Faries et al. | |
| 6,843,099 B2 | 1/2005 | Derek et al. | |
| 6,896,664 B2 | 5/2005 | Novak | |
| 7,083,601 B1* | 8/2006 | Cosmescu | A61M 1/743 604/289 |
| 7,207,966 B2 | 4/2007 | Savare et al. | |
| 7,981,073 B2 | 7/2011 | Möllstam et al. | |
| 8,444,592 B2 | 5/2013 | Williams et al. | |
| 8,597,228 B2 | 12/2013 | Pyles et al. | |
| 8,790,303 B2 | 7/2014 | Williams et al. | |
| 8,795,232 B2* | 8/2014 | Visconti | A61M 1/72 604/131 |
| 9,272,086 B2 | 3/2016 | Williams et al. | |
| 9,474,848 B2 | 10/2016 | Williams et al. | |
| 9,770,541 B2 | 9/2017 | Carr et al. | |
| 9,962,472 B2 | 5/2018 | Woolford et al. | |
| 10,077,767 B2 | 9/2018 | Macari et al. | |
| 2002/0032403 A1 | 3/2002 | Savagle et al. | |
| 2003/0004470 A1 | 1/2003 | Hickerson et al. | |
| 2003/0216689 A1 | 11/2003 | Bouhuijs et al. | |
| 2004/0170409 A1 | 9/2004 | Faries, Jr. et al. | |
| 2004/0260232 A1* | 12/2004 | Cimino | A61M 3/022 604/151 |
| 2007/0265689 A1 | 11/2007 | Frey | |
| 2013/0197471 A1* | 8/2013 | Williams | A61M 5/365 604/247 |
| 2014/0171770 A1* | 6/2014 | Hann | A61B 5/0205 604/510 |
| 2014/0303551 A1* | 10/2014 | Germain | A61M 3/0208 606/115 |
| 2017/0027637 A1 | 2/2017 | Germain et al. | |
| 2017/0055810 A1 | 3/2017 | Germain et al. | |
| 2017/0184088 A1 | 6/2017 | Macari et al. | |
| 2018/0000998 A1 | 1/2018 | Carr et al. | |
| 2018/0207332 A1* | 7/2018 | Reever | A61M 1/743 |
| 2018/0361055 A1 | 12/2018 | Pereira et al. | |
| 2019/0060546 A1* | 2/2019 | Callaghan | A61B 5/6852 |
| 2019/0120223 A1 | 4/2019 | Macari et al. | |
| 2020/0121848 A1 | 4/2020 | Schmidlin et al. | |
| 2020/0146703 A1* | 5/2020 | Truckai | A61B 1/045 |
| 2020/0237977 A1* | 7/2020 | Panotopoulos | A61B 5/031 |
| 2020/0297900 A1* | 9/2020 | Holigan | A61M 3/0208 |
| 2020/0405955 A1 | 12/2020 | Shah et al. | |
| 2022/0142806 A1* | 5/2022 | Passman | A61M 3/0279 |

FOREIGN PATENT DOCUMENTS

| | | |
|---|---|---|
| CN | 105377159 A | 3/2016 |
| WO | 8700759 A1 | 2/1987 |
| WO | 9217040 A1 | 10/1992 |
| WO | 9322979 A1 | 11/1993 |
| WO | 9640331 A1 | 12/1996 |
| WO | 9716220 A1 | 5/1997 |
| WO | 97046271 A1 | 12/1997 |
| WO | 2013110073 A1 | 7/2013 |
| WO | 2014164655 A1 | 10/2014 |
| WO | 2018236513 A1 | 12/2018 |

* cited by examiner

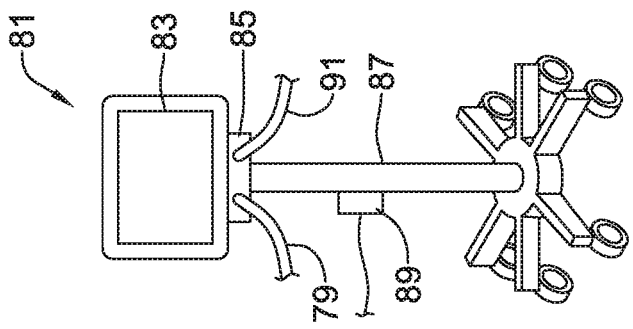
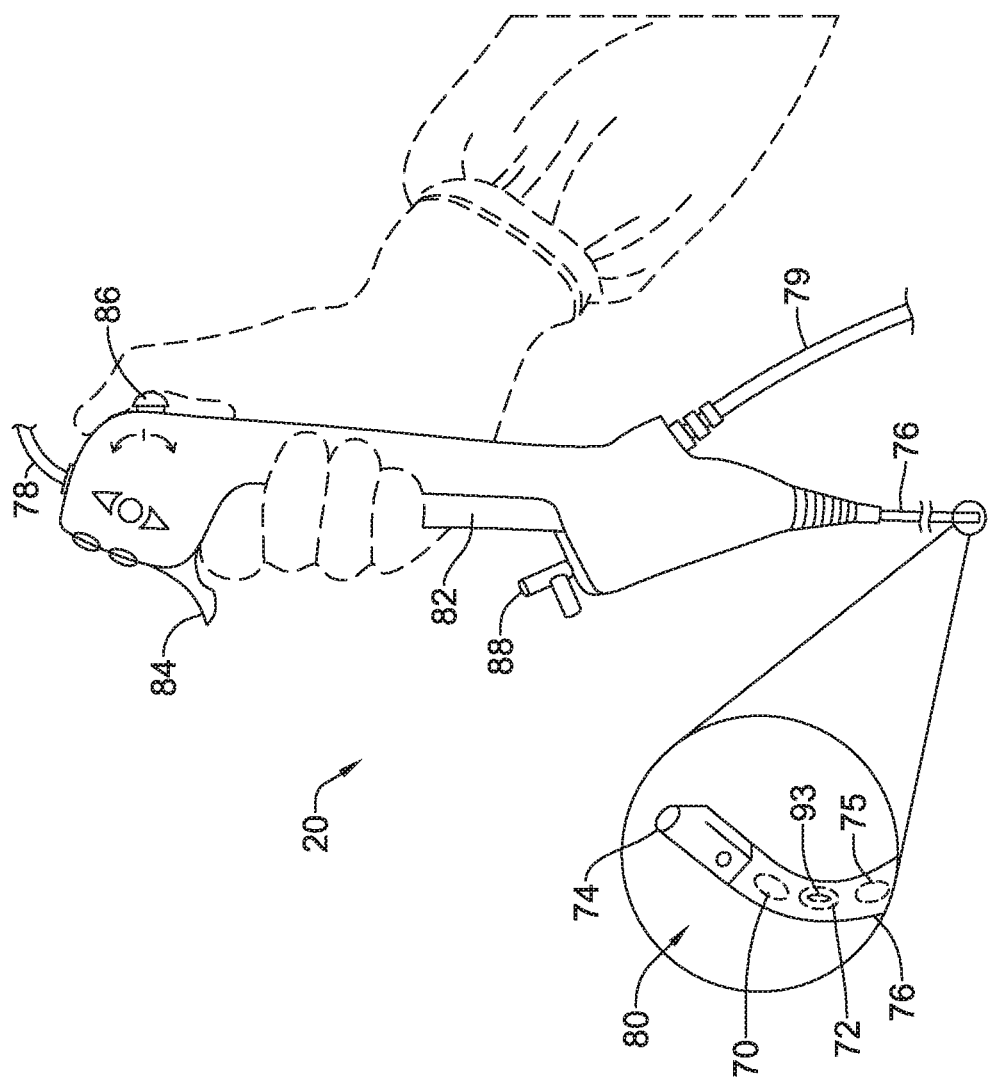
FIG. 2

SYSTEM AND METHOD FOR MONITORING FLUID DEFICIT

CROSS-REFERENCE TO RELATED APPLICATIONS

This application claims the benefit of priority under 35 U.S.C. § 119 of U.S. Provisional Application No. 62/928, 005 filed Oct. 30, 2019, the entire disclosure of which is hereby incorporated by reference.

TECHNICAL FIELD

The disclosure is directed to a fluid management system. More particularly, the disclosure is directed to a system and method for monitoring a fluid deficit in and/or with a fluid management system.

BACKGROUND

Flexible ureteroscopy (fURS), gynecology, and other endoscopic procedures require the circulation of fluid for several reasons. Surgeons today deliver the fluid in various ways such as, for example, by hanging a fluid bag and using gravity to deliver the fluid, filling a syringe and manually injecting the fluid or using a peristaltic pump to deliver fluid from a reservoir at a fixed pressure or flow rate via a fluid management system. Fluid management systems may adjust the flow rate and/or pressure at which fluid is delivered from the reservoir based on data collected from a procedural device, such as, but not limited to, an endoscope. Of the known medical devices, systems, and methods, each has certain advantages and disadvantages. There is an ongoing need to provide alternative medical devices and fluid delivery systems.

SUMMARY

In a first example, a fluid management and medical device system may comprise a medical device comprising: an elongate shaft configured to access a treatment site within a patient; one or more sensors proximate a distal end of the elongate shaft; and a handle coupled to a proximal end of the elongate shaft. The fluid management and medical device system may also comprise a fluid management system comprising: an inflow pump configured to pump fluid from a fluid supply source to the treatment site; and a controller configured to calculate a fluid deficit when the distal end of the elongate shaft is disposed within the patient. The controller may be configured to automatically pause fluid deficit calculation when the distal end of the elongate shaft is removed from the patient.

In addition or alternatively to any example disclosed herein, the controller may be configured to resume fluid deficit calculation when signals from the one or more sensors indicate the distal end of the elongate shaft is reinserted into the patient.

In addition or alternatively to any example disclosed herein, the controller may be configured to control the inflow pump to maintain a target fluid flow rate or target fluid pressure based on a set of system operating parameters.

In addition or alternatively to any example disclosed herein, the controller may be configured to automatically reset the fluid deficit to zero after priming of the fluid management system.

In addition or alternatively to any example disclosed herein, the controller may be configured to automatically begin fluid deficit calculation when signals from the one or more sensors indicate the distal end of the elongate shaft is inserted within the patient.

In addition or alternatively to any example disclosed herein, the one or more sensors includes a temperature sensor.

In addition or alternatively to any example disclosed herein, the one or more sensors includes a pressure sensor.

In addition or alternatively to any example disclosed herein, the one or more sensors includes a temperature sensor and a pressure sensor.

In addition or alternatively to any example disclosed herein, the fluid management system includes a vacuum pump and a collection container in fluid communication with a collection drape.

In addition or alternatively to any example disclosed herein, fluid deficit calculation continues uninterrupted when the fluid supply source is replenished.

In addition or alternatively to any example disclosed herein, and in a second example, a fluid management and medical device system may comprise a medical device comprising: an elongate shaft configured to access a treatment site within a patient; one or more sensors proximate a distal end of the elongate shaft; and a handle coupled to a proximal end of the elongate shaft. The fluid management and medical device system may also comprise a fluid management system comprising: a fluid supply source operatively coupled to a supply load cell and in fluid communication with the elongate shaft; a collection container operatively coupled to a collection load cell and in fluid communication with a collection drape; an inflow pump configured to pump fluid from the fluid supply source to the treatment site; and a controller configured to control the inflow pump to maintain a desired fluid pressure at the treatment site or a desired fluid flow rate based on a set of system operating parameters. The controller may be in electronic communication with the supply load cell and the collection load cell. The controller may be configured to calculate a fluid deficit using rotational speed of the inflow pump in combination with a difference between a change in weight of the fluid supply source and a change in weight of the collection container.

In addition or alternatively to any example disclosed herein, the controller may be configured to calculate the fluid deficit only when the distal end of the elongate shaft is disposed within the patient.

In addition or alternatively to any example disclosed herein, the controller may be configured to automatically pause fluid deficit calculation when the distal end of the elongate shaft is removed from the patient.

In addition or alternatively to any example disclosed herein, the controller may be configured to calculate a first fluid deficit value using a flow rate of the fluid and a second fluid deficit value using the difference between the change in weight of the fluid supply source and the change in weight of the collection container. A displayed deficit value may be based on a combination of the first fluid deficit value and the second fluid deficit value.

In addition or alternatively to any example disclosed herein, the flow rate of the fluid is determined using the rotational speed of the inflow pump.

In addition or alternatively to any example disclosed herein, the flow rate of the fluid is determined using data from a flow sensor disposed between the fluid supply source and the treatment site.

In addition or alternatively to any example disclosed herein, the controller may be configured to display the displayed deficit value if a difference between the first fluid deficit value and the second fluid deficit value is within a predetermined range. The controller may be configured to display a notification if the difference between the first fluid deficit value and the second fluid deficit value is outside of the predetermined range.

In addition or alternatively to any example disclosed herein, and in a third example, an automated fluid management system may comprise a medical device comprising: an elongate shaft configured to access a treatment site within a patient; one or more sensors proximate a distal end of the elongate shaft; and a handle coupled to a proximal end of the elongate shaft. The automated fluid management system may also comprise a fluid management system comprising: a first fluid supply source in fluid communication with the elongate shaft; a second fluid supply source; a collection container in fluid communication with the elongate shaft; an inflow pump configured to pump fluid from the first fluid supply source to the treatment site; and a controller configured to set a total fluid deficit to zero after priming the fluid management system. The controller may be configured to automatically begin calculating a first fluid deficit associated with the first fluid supply source when the distal end of the elongate shaft is disposed within the patient. The controller may be configured to retain the first fluid deficit when the first fluid supply source is replaced with the second fluid supply source in fluid communication with the elongate shaft, and the controller may be configured to thereafter calculate the total fluid deficit by adding the first fluid deficit and a second fluid deficit associated with the second fluid supply source when the distal end of the elongate shaft is disposed within the patient.

In addition or alternatively to any example disclosed herein, the controller may be configured to notify a user when the total fluid deficit reaches a preset fluid deficit limit.

In addition or alternatively to any example disclosed herein, the controller may be configured to automatically pause fluid deficit calculation when the distal end of the elongate shaft is removed from the patient.

In addition or alternatively to any example disclosed herein, the controller may be configured to automatically resume fluid deficit calculation when the distal end of the elongate shaft is reinserted into the patient.

In addition or alternatively to any example disclosed herein, the controller may be configured to detect signals from the one or more sensors to determine when the distal end of the elongate shaft is disposed within the patient.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The invention may be more completely understood in consideration of the following detailed description in connection with the accompanying drawings, in which:

FIG. 2 illustrates selected aspects of a medical device and a workstation of the system of FIG. 1;

Figure 1:
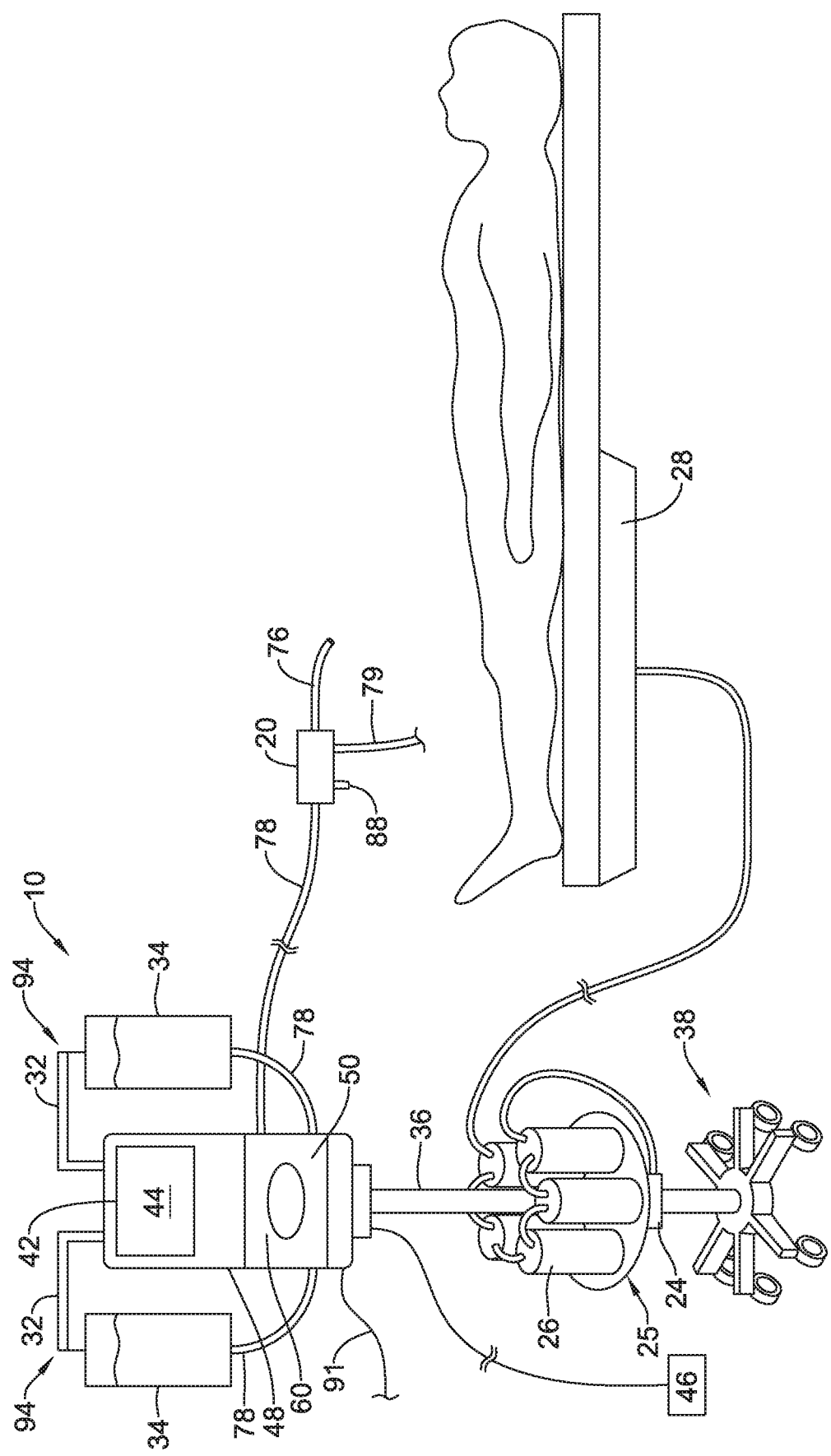
FIG. 1 is a schematic illustration of selected aspects of a fluid management system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some fluid management systems for use in flexible ureteroscopy (fURS) procedures (e.g., ureteroscopy, percutaneous nephrolithotomy (PCNL), benign prostatic hyperplasia (BPH), transurethral resection of the prostate (TURP), etc.), gynecology, and other endoscopic procedures may regulate body cavity pressure when used in conjunction with an endoscope device such as, but not limited to, a Litho-Vue™ scope device using pressure and/or temperature data from the endoscope or other endoscopic device. Direct regulation of the intracavity pressure during a medical procedure may allow the fluid management system to safely drive system pressures of up to 600 mmHg to ensure no loss of flow during the procedure when tools are inserted into the working channel of the endoscope device. Fluid deficit may be a concern for physicians, for example during lengthy and/or heavy fluid usage procedures. Excess fluid absorption by the patient may cause serious complications such as edema/water intoxication and/or sepsis condition, for example during BPH/TURP at high pressure and/or in high volume cases. An acceptable loss of fluid (e.g., fluid deficit) may be difficult to determine as it may vary from patient to patient and procedure to procedure. Additionally, keep track of the amount of fluid infused may be difficult as numerous fluid supply sources (e.g., bags of saline, glycine, etc.) may be used during a procedure. Fluid deficit may also be difficult to calculate due to its dependence on the waste collection system, because fluid lost outside of the collection system (e.g., on the floor, for example) may escape inclusion in the calculation. As a result, in some procedures, the fluid deficit is estimated and may be inaccurate. Systems and methods that automate and/or improve the accuracy of fluid deficit calculation and/or monitoring are desired.

FIG. 1 is a schematic view of a fluid management system 10 that may be used in an endoscopic procedure, such as fURS procedures. The fluid management system 10 may be coupled to a medical device 20 that allows flow of fluid therethrough and includes a pressure sensor. An illustrative medical device 20 may be a LithoVue™ scope device, or other endoscope. In an illustrative embodiment, the medical device 20 may include a temperature sensor to provide intracavity temperature feedback to the fluid management system 10, a pressure sensor to provide intracavity pressure feedback to the fluid management system 10, and/or a camera to provide visual feedback to the fluid management system 10.

Briefly, the fluid management system 10 may include an inflow pump 50 configured to pump and/or transfer fluid from a fluid supply source 34 (e.g., a fluid bag, etc.) to the medical device 20 and/or the treatment site. In some cases, the fluid may pass through a fluid warming system 60 prior to entering the medical device 20. The flow of fluid, pressure of the fluid, temperature of the fluid, and other operational parameters may be controlled by or at least partially controlled by a controller 48. The controller 48 may be in electronic communication (e.g., wired or wireless) with the medical device 20, the inflow pump 50, and/or the fluid warming system 60 to provide control commands and/or to transfer or receive data therebetween. For example, as will be described in more detail herein, the controller 48 may receive data from the medical device 20, such as, but not limited to, pressure and temperature data. The controller 48 may then use the data received from the medical device 20 to control operational parameters of the inflow pump 50 and/or the fluid warming system 60. In some embodiments, the controller may be configured to control the inflow pump 50 to maintain a target fluid flow rate or target fluid pressure based on a set of system operating parameters. In some embodiments, the controller 48 may be configured to control the inflow pump 50 to maintain a desired fluid pressure at the treatment site or a desired flow rate based on a set of system operating parameters.

The fluid management system 10 also includes a fluid management unit. An illustrative fluid management unit may include one or more fluid container supports, such as fluid supply source hanger(s) 32, each of which supports one or more fluid supply sources 34 (e.g., one or more fluid bags). In some embodiments, placement and/or weight of the fluid supply source 34 (e.g., the fluid bag) may be detected using a remote sensor and/or a supply load cell 94 associated with and/or operatively coupled to each fluid supply source hanger 32 and/or fluid container support. The controller 48 may be in electronic communication with the supply load cell 94. The fluid supply source hanger(s) 32 may receive a variety of sizes of fluid supply sources 34 such as, for example, 1 liter (L) to 5 L fluid supply sources (e.g., fluid bags). It will be understood that any number of fluid supply sources 34 may be used. Furthermore, fluid supply sources 34 of any size may be used depending on the procedure. In some embodiments, the fluid management unit may be mounted to a rolling stand, which may include a pole 36 and/or a base 38. The base 38 may include a plurality of wheels to facilitate easy movement of the fluid management unit when in use. However, it will be understood that the fluid supply source 34 may also be hung from the ceiling or other location depending on the clinical preference. The fluid supply source hanger(s) 32 may extend from the pole 36 and/or the controller 48 and may include one or more hooks from which one or more fluid supply sources 34 may be suspended. In some embodiments, the fluid used in the fluid management unit may be 0.9% saline. However, it will be understood that a variety of other fluids of varying viscosities may be used depending on the procedure.

In some embodiments, the fluid management unit may include a vacuum pump 24 and a collection container 26 in fluid communication with a collection drape 28. In some embodiments, the vacuum pump 24 may include a plurality of vacuum pumps. In some embodiments, the collection container 26 may include a plurality of containers, canisters, and/or other receptacles, which may be fluidly connected to each other and/or the vacuum pump 24. In some embodiments, the collection drape 28 may include a plurality of collection drapes. The vacuum pump 24 may be operatively and/or electronically connected to the controller 48. In some embodiments, the vacuum pump 24 may be disposed adjacent to and/or near the collection container 26, as illustrated in FIG. 1. In some embodiments, the vacuum pump 24 may be disposed within the fluid management system 10. Other configurations are also contemplated. In some embodiments, the collection container 26 may be operatively coupled to a collection load cell 25 to detect placement and/or weight of the collection container 26. In embodiments having a plurality of containers, canisters, and/or other receptacles, each container, canister, and/or receptacle may be operatively coupled to a corresponding collection load cell 25. The controller 48 may be in electronic communication with the collection load cell(s) 25.

The fluid management system 10 may also include one or more user interface components such as a touch screen interface 42. The touch screen interface 42 includes a display screen 44 and may include switches or knobs in addition to touch capabilities. In some embodiments, the controller 48 may include the touch screen interface 42 and/or the display screen 44. The touch screen interface 42 allows the user to input/adjust various functions of the fluid management system 10 such as, for example flow rate, pressure or temperature. The user may also configure parameters and alarms (such as, but not limited to, a max pressure alarm), information to be displayed, and the procedure mode. The touch screen interface 42 allows the user to add, change, and/or discontinue the use of various modular systems within the fluid management system 10. The touch screen interface 42 may also be used to change the fluid management system 10 between automatic and manual modes for various procedures. It is contemplated that other systems configured to receive user input may be used in place of or in addition to the touch screen interface 42.

The touch screen interface 42 may be configured to include selectable areas like buttons and/or may provide a functionality similar to physical buttons as would be understood by those skilled in the art. The display screen 44 may be configured to show icons related to modular systems and devices included in the fluid management system 10. The display screen 44 may also include a flow rate display. The flow rate display may be determined based on a desired threshold for flow rate set by the user prior to the procedure or based on known common values, etc. In some embodiments, the operating parameters may be adjusted by touching the corresponding portion of the touch screen interface 42. The touch screen interface 42 may also display visual alerts and/or audio alarms if parameters (e.g., flow rate, temperature, etc.) are above or below predetermined thresholds and/or ranges. The touch screen interface 42 may also be configured to display the amount of fluid remaining in the fluid supply source 34, and/or any other information the user may find useful during the procedure. In some embodiments, the fluid management system 10 may also include further user interface components such as an optional foot pedal 46, a heater user interface, a fluid control interface, or other device to manually control various modular systems. For example, the optional foot pedal 46 may be used to manually control flow rate. Some illustrative display screens 44 and other user interface components are described in described in commonly assigned U.S. Patent Application Publication No. 2018/0361055, titled AUTOMATED FLUID MANAGEMENT SYSTEM, the entire disclosure of which is hereby incorporated by reference.

The touch screen interface 42 may be operatively connected to or a part of the controller 48. The controller 48 may be a computer, tablet computer, or other processing device. The controller 48 may be operatively connected to one or more system components such as, for example, the inflow pump 50, the fluid warming system 60, and a fluid deficit management system. In some embodiments, these features may be integrated into a single unit. The controller 48 is capable of and configured to perform various functions such as calculation, control, computation, display, etc. The controller 48 is also capable of tracking and storing data pertaining to the operations of the fluid management system 10 and each component thereof. In an illustrative embodiment, the controller 48 includes wired and/or wireless network communication capabilities, such as ethernet or Wi-Fi, through which the controller 48 may be connected to, for example, a local area network. The controller 48 may also receive signals from one or more of the sensors of the fluid management system 10. In some embodiments, the controller 48 may communicate with databases for best practice suggestions and the maintenance of patient records which may be displayed to the user on the display screen 44.

The fluid management system 10 may be user selectable between different modes based on the procedure, patient characteristics, etc. For example, different modes may include, but are not limited to, fURS Mode, BPH Mode, Hysteroscopy Mode, Cystoscopy Mode, etc. Once a mode has been selected by the user, mode parameters such as fluid flow rate, fluid pressure, fluid deficit, and temperature may be provided to the user via the display screen. The exemplary parameters of the specific modes may be previously determined and loaded onto the controller 48 using, for example, software. Thus, when a user selects a procedure from an initial display on the touch screen interface display screen 44 (e.g., FIG. 7), these known parameters may be loaded from the controller 48 to the various components of the fluid management system 10, such as, but not limited to the inflow pump 50, the fluid warming system 60, the fluid deficit management system, etc. The fluid management system 10 may also be user selectable between automatic and manual mode. For example, for certain procedures, the user may wish to manually adjust a fluid flow rate, fluid pressure, and/or other parameters. Once the user has selected the manual mode on, for example, the touch screen interface 42, the user may the adjust fluid flow rate or fluid pressure via other manual interfaces such as the optional foot pedal 46 or the fluid control interface. If the user selects an automatic mode, the user may be prompted to select or input via the touch screen interface 42 which medical device 20 is being used so that the controller 48 may determine if data obtained from the medical device 20 can be used to facilitate control of the fluid management system 10. As will be described in more detail herein, the fluid management system 10 may be configured to verify the medical device 20 selected is actually being used prior to using the collected data.

The controller 48 may be configured to include visual software/image recognition software that can detect visual noise based on variations in brightness (e.g., light monitoring), contrast, or color pixilation. If the image provided to the controller 48 is determined to be not sufficiently clear or sharp, the fluid management system 10 may increase the fluid flow rate or the fluid pressure to flush out debris from the treatment site to sharpen/clear the image. The fluid flow rate or the fluid pressure may be increased for a temporary time (e.g., a predetermined time period) or until the field of view is deemed to be sufficiently clear. This temporary increase ensures that the time at which the fluid flow rate or the fluid pressure is increased is limited to ensure that intracavity pressure does not exceed safe limits. For example, the fluid management system 10 may recognize a red hue in the irrigation (a sign of blood) and signal to the inflow pump 50 to increase the fluid flow rate or the fluid pressure until the blood is cleared from the field of view. Alternatively, the controller 48 may provide a visual alert on the display screen 44 or an audible alert to the physician or nurse that a cloudy view has been detected and the user may then adjust the irrigation flow rate manually. In another example, in instances where there is a significant amount of debris, light reflected from the debris may brighten the image substantially. In this situation, the controller 48 detects this inordinate brightness and signals to the inflow pump 50 to increase the fluid flow rate or the fluid pressure to flush away and/or remove debris. Once the reflected light has been reduced as the debris is flushed clear of the field of view of the vision system, the inflow pump 50 is controlled by the controller 48 to reduce the fluid flow rate or the fluid pressure. In some cases, the physician may create a baseline level for visibility at which he or she prefers to initiate a field clearing flow of fluid and input these parameters into the fluid management system 10 via the touch screen interface 42 prior to the procedure. Once the baseline has been created, the fluid management system 10 may monitor the visual feed for variation in the picture and automatically adjust the fluid flow rate as necessary.

In order to adjust the fluid flow rate or the fluid pressure through the fluid management system 10, the fluid management unit may include one or more pressurization devices such as the inflow pump 50. In some embodiments, the inflow pump 50 may be a peristaltic pump. In some embodiments, the inflow pump 50 may include multiple pumps or more than one pump. The inflow pump 50 may be electrically driven and may receive power from a line source such as a wall outlet, an external or internal electrical storage device such as a disposable or rechargeable battery, and/or an internal power supply. The inflow pump 50 may operate at any desired speed sufficient to deliver fluid at a target pressure such as, for example, 5 mmHg to 50 mmHg, and/or at a target fluid flow rate or a target fluid pressure. As noted herein, the inflow pump 50 may be automatically adjusted based on, for example, pressure and/or temperature readings within the treatment site and/or visual feedback from the medical device 20. The inflow pump 50 may also be manually adjusted via, for example, the optional foot pedal 46, the touch screen interface 42, or a separate fluid controller. While not explicitly shown, the fluid controller may be a separate user interface including buttons that allow the user to increase or decrease the inflow pump 50. Alternatively, the fluid controller may be incorporated into the main processing device and receive input via the touch screen interface 42. It will be understood that any number of pumps may be used. In some embodiments, the fluid management system 10 may include multiple pumps having different flow capabilities. In some embodiments, a flow meter may be located before and/or after the inflow pump 50.

The fluid flow rate or the fluid pressure of the fluid at any given time may be displayed on the display screen 44 to allow the operating room (OR) visibility for any changes. If the OR personnel notice a change in fluid flow rate or fluid pressure that is either too high or too low, the user may manually adjust the fluid flow rate or the fluid pressure back to a preferred level. This may happen, for example, as physicians insert and remove tools into the working channel of the medical device 20. The fluid management system 10 may also monitor and automatically adjust the fluid flow rate or the fluid pressure based on previously set parameters, as discussed herein. This feature may also be beneficial when fluid flow is provided manually such as an assistant injecting irrigation through a syringe.

In some embodiments, the fluid management system 10 may include visual software or image recognition and analysis software. For example, the fluid management system 10 may detect, via a camera 70 (see, for example, FIGS. 2 and 3) positioned on the medical device 20 within the body, whether a tool has been inserted or not and which tool is being used. The tool may, for example, have an identifiable marker that the visual software may see to inform the fluid management system 10 what type of tool is being used. The fluid management system 10 may then automatically adjust the fluid flow rate or the fluid pressure based on the tool identified by the visual software. When the tool is retracted from the working channel, the fluid management system 10 may automatically reduce the fluid flow rate or the fluid pressure accordingly.

Additionally, or alternatively, the fluid management system 10 may automatically adjust the fluid flow rate or the fluid pressure based on an intracavity temperature and/or pressure detected within the treatment site. The intracavity temperature and/or pressure may be measured in situ using a temperature sensor 72 and/or a pressure sensor 74 mounted on the medical device 20, used in conjunction with the fluid management system 10. The fluid management system 10 may include pressure monitoring software so that the inflow pump 50 may be configured by the user to be automatically started, stopped, and/or speed adjusted by the fluid management system 10 to maintain a fluid pressure delivered to the treatment site at a target pressure and/or within a predetermined pressure range. For example, the pressure sensor 74 may detect pressure within the treatment site (for example, a kidney or uterus) and automatically alter the fluid flow rate or the fluid pressure within the fluid management system 10 based on a monitored intracavity (e.g., intrarenal or intrauterine) pressure. If the intracavity pressure is too high, the fluid management system 10 may decrease the fluid flow rate or the fluid pressure and if the intracavity pressure is too low, the fluid management system 10 may increase the fluid flow rate or the fluid pressure. In an exemplary temperature control mode, the fluid management system 10 may include temperature monitoring software so that the fluid warming system 60 may be controlled (e.g., started, stopped, and temperature adjusted) to maintain a fluid temperature delivered to a treatment site at about a target temperature and/or within a predetermined temperature range. For example, the temperature may be monitored in vivo or in vitro and the flow of fluid altered based on the temperature feedback provided. In an illustrative embodiment, the fluid management system 10 may compare the temperature and/or pressure sensed within the treatment site to known values and provide a warning when the parameters are outside of a predetermined safe range. The warning may be a visual or audio alert.

In some embodiments, the fluid management system 10 may monitor movement of a target structure or object such as, for example, a kidney stone. The fluid management system 10 may calculate the rate of movement based on the original position of the target structure or object and its new position. If the movement exceeds a predetermined threshold, the user may be alerted to manually adjust the fluid flow rate or the fluid pressure of the fluid management system 10. As described herein, the fluid flow rate or the fluid pressure may be adjusted manually via the optional foot pedal 46, the touch screen interface 42, and/or a pump interface. In some embodiments, if the fluid management system 10 is in an automatic mode, the fluid management system 10 will automatically adjust the fluid flow rate or the fluid pressure as necessary automatically. This capability may be extremely beneficial during procedures such as a lithotripsy to control retropulsion of the target structure or object.

Figure 3:
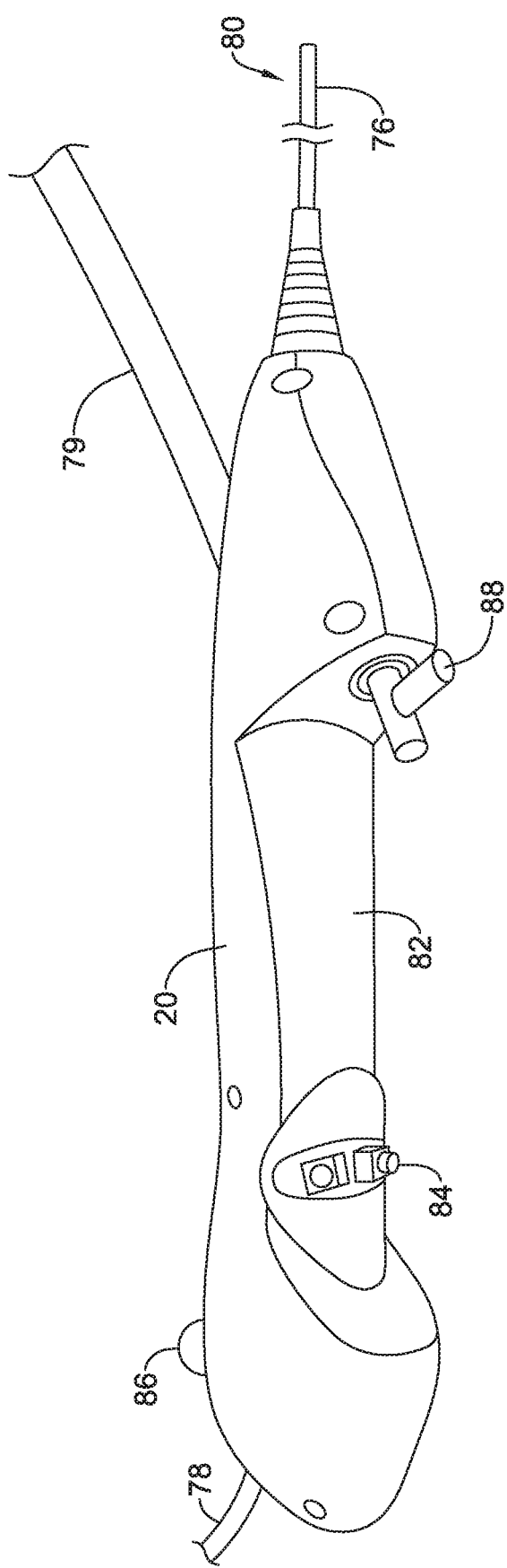
FIG. 3 illustrates selected aspects of the medical device of FIG. 2.
Figure 4:
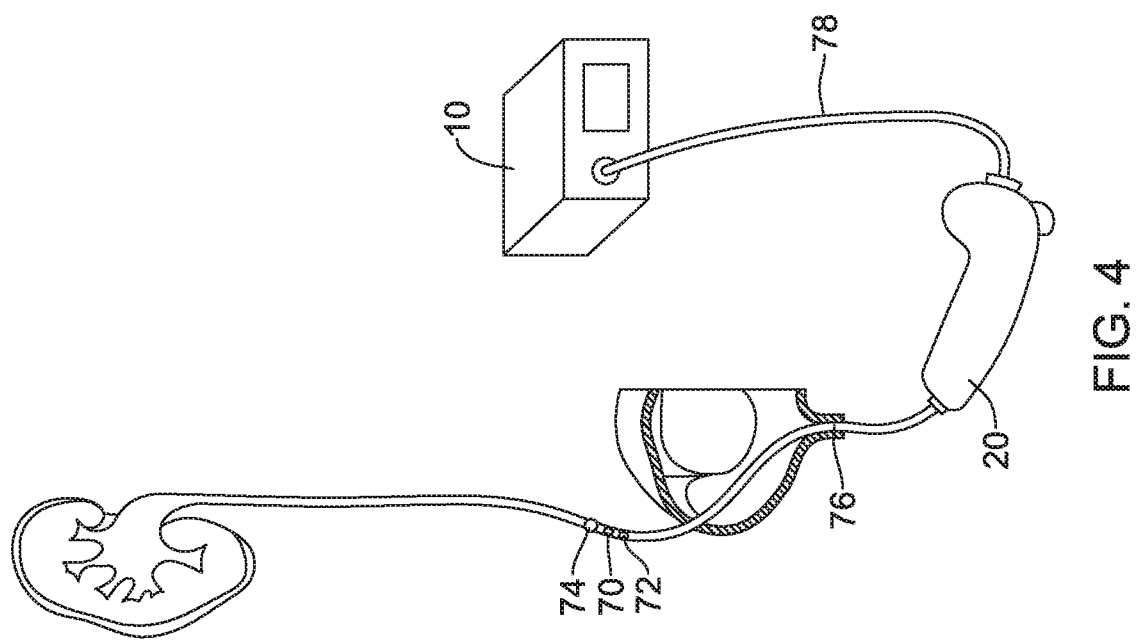
FIG. 4 is a schematic illustration of the medical device of FIG. 2 in situ.

FIGS. 2-4 illustrate aspects of the medical device 20 that may be used in conjunction with the fluid management system 10. In the illustrated embodiments, the medical device 20 may be a ureteroscope such as a LithoVue™ scope. However, other medical devices, such as another endoscope, may be used in addition to or in place of a ureteroscope. The medical device 20 may be configured to deliver fluid from the fluid management system 10 to the treatment site via an elongate shaft 76 configured to access the treatment site within the patient. In some embodiments, the inflow pump 50 may be in fluid communication with the elongate shaft 76. The elongate shaft 76 may include one or more working lumens for receiving a flow of fluid or other medical devices therethrough. The medical device 20 is connected to the fluid management system 10 via one or more supply line(s) 78 (e.g., a tube), as shown in FIG. 4, which is a schematic view of the medical device 20 in fluid communication with the fluid management system 10 and positioned within a patient's body.

In some embodiments, the medical device 20 may be in electronic communication with a workstation 81 via a wired connection 79. The workstation 81 may include a touch panel computer 83, an interface box 85 for receiving the wired connection 79, a cart 87, and a power supply 89, among other features. In some embodiments, the interface box 85 may be configured with a wired or wireless communication connection 91 with the controller 48 of the fluid management system 10. The touch panel computer 83 may include at least a display screen and an image processor. In some embodiments, the workstation 81 may be a multi-use component (e.g., used for more than one procedure) while the medical device 20 may be a single use device, although this is not required. In some embodiments, the workstation 81 may be omitted and the medical device 20 may be electronically coupled directly to the controller 48 of the fluid management system 10.

The one or more supply line(s) 78 from the fluid management system 10 to the medical device 20 may be formed of a material the helps dampen the peristaltic motion created by the inflow pump 50. Returning now to FIG. 2, the medical device 20 may include one or more sensors proximate a distal end 80 of the elongate shaft 76. For example, the medical device 20 may include a pressure sensor 74 at a distal tip of the elongate shaft 76 to measure intracavity pressure within the treatment site. The medical device 20 may also include other sensors such as, for example, a temperature sensor 72, a Fiber Bragg grating optical fiber 75 to detect stresses, and/or an antenna or electromagnetic sensor 93 (e.g., a position sensor). In an illustrative embodiment, the distal end 80 of the medical device 20 may also include at least one camera 70 to provide a visual feed to the user on the display screen of the touch panel computer 83. In another embodiment, the medical device 20 may include two cameras 70 having different communications requirements or protocols so that different information may be relayed to the user by each camera 70. When so provided, the user may switch back and forth between cameras 70 at will through the touch screen interface 42 and/or the touch panel computer 83. While not explicitly shown, the elongate shaft 76 may include one or more working lumens for receiving the fluid and/or other medical devices.

The medical device 20 includes a handle 82 coupled to a proximal end of the elongate shaft 76. The handle 82 may have a fluid flow on/off switch 84, which allows the user to control when fluid is flowing through the medical device 20 and into the treatment site. The handle 82 may further include other buttons 86 that perform other various functions. For example, in some embodiments, the handle 82 may include buttons to control the temperature of the fluid.

In some embodiments, the handle 82 may include a laser so that the user may fire laser energy. In an illustrative embodiment, the laser may be a Lumenis or StarMed Tech Laser. A laser fiber may be connected to the laser system and inserted through the ureteroscope working channel. The user may fire the laser so that energy comes out of the tip of the laser fiber and hits the debris/stone to break it up. In an exemplary embodiment including a laser button on the handle 82, a communication line between the laser system and the handle 82 is maintained (e.g., hardwire or wireless). It will be understood that while the exemplary embodiment describes a ureteroscope, the features detailed above may also be directly integrated into a cystoscope, an endoscope, a hysteroscope, or virtually any device with an image capability. In some embodiments, the medical device 20 may also include a drainage port 88 which may be connected to a drainage system. Some illustrative drainage systems are described in commonly assigned U.S. Patent Application Publication No. 2018/0361055, titled AUTOMATED FLUID MANAGEMENT SYSTEM, the disclosure of which is hereby incorporated by reference.

Returning briefly to FIG. 1, the controller 48 may be configured to calculate a fluid deficit when the distal end 80 of the elongate shaft 76 is disposed within the patient, the fluid deficit being representative of fluid lost, absorbed by the patient, and/or otherwise unaccounted for during a procedure.

Prior to starting the procedure, the fluid management system 10 may need to be primed to remove any air from the system. Priming the fluid management system 10 may result in some fluid being lost. In some embodiments, the controller 48 may be configured to automatically reset the fluid deficit to zero after priming of the fluid management system 10. In some embodiments, the controller 48 may be configured to automatically begin fluid deficit calculation when signals from the one or more sensors indicate the distal end 80 of the elongate shaft 76 is inserted within the patient. In some embodiments, the controller 48 may be configured to automatically pause fluid deficit calculation when the distal end 80 of the elongate shaft 76 is removed from the patient. Additional details regarding systems and methods to detect when the distal end 80 of the elongate shaft 76 of the medical device 20 is disposed within the patient are discussed below. In some embodiments, the controller 48 may be configured to automatically resume fluid deficit calculation when signals from the one or more sensors indicate the distal end 80 of the elongate shaft 76 is reinserted into the patient. In some embodiments, the controller 48 may be configured to calculate the fluid deficit only when the distal end 80 of the elongate shaft 76 is disposed within the patient.

In an alternative embodiment, fluid deficit calculation may begin after initial set-up of the system (e.g., prior to priming). After set-up, the controller 48 may be placed into a "Priming Mode". The controller 48 may be configured to monitor fluid used during priming of the system (e.g., "Priming Mode"). The fluid used during priming may be determined using pump rotation speed, flow sensor data, weight change of the fluid supply source 34, or other suitable means. After priming of the system, the controller 48 may be placed into an "Operation Mode". The fluid used during priming of the system may be excluded from the fluid deficit calculation and/or may be subtracted from the calculated fluid deficit to determine a true fluid deficit. For example, the supply line(s) 78 and/or the heater cassette 64 may define and/or contain a known fluid volume. The controller 48 may be configured to exclude the known fluid volume of the supply line(s) 78 and/or the heater cassette 64 from the fluid deficit calculation.

Additionally, in some embodiments, fluid deficit calculation may continue uninterrupted when the fluid supply source 34 is replenished. For example, if the fluid supply source 34 is replaced or refilled during the procedure, the same procedure continues. As such, the fluid deficit being calculated by the controller 48 may also continue to maintain a total fluid deficit for the entire procedure. Accordingly, in some embodiments, the fluid management system 10 may include a first fluid supply source 34 in fluid communication with the elongate shaft 76 and a second fluid supply source 34. The controller 48 may be configured to set a total fluid deficit to zero after priming the fluid management system 10. In use, the controller 48 may be configured to automatically begin calculating a first fluid deficit associated with the first fluid supply source 34 when the distal end 80 of the elongate shaft 76 is disposed within the patient. During the procedure, if the first fluid supply source 34 runs low or runs out, it may be replaced, refilled, and/or replenished by the second fluid supply source 34. The controller 48 may be configured to retain the first fluid deficit when the first fluid supply source 34 is replaced with the second fluid supply source 34 in fluid communication with the elongate shaft 76, and the controller 48 may be configured to thereafter calculate the total fluid deficit by adding the first fluid deficit to a second fluid deficit associated with the second fluid supply source 34 when the distal end 80 of the elongate shaft 76 is disposed within the patient.

In some embodiments, the controller 48 may be configured to notify a user when the total fluid deficit reaches a preset fluid deficit limit. In some embodiments, the controller 48 may be configured to stop the inflow pump 50 and/or the vacuum pump 24 when the total fluid deficit reaches the preset fluid deficit limit.

In some embodiments, the controller 48 may be configured to notify a user when a total amount of fluid infused reaches a preset fluid infusion limit. In some embodiments, the controller 48 may be configured to stop the inflow pump 50 and/or the vacuum pump 24 when the total amount of fluid infused reaches the preset fluid infusion limit.

In some embodiments, the controller 48 may be configured to monitor the amount of fluid in the fluid supply source 34 through weight using, for example, the supply load cell 94, a scale, or other suitable means. The supply load cell 94 may be used by the controller 48 to determine a weight of the fluid supply source 34 attached to the fluid supply source hanger 32 to compare an initial amount of fluid in the fluid supply source 34 to a current amount of fluid remaining in the fluid supply source 34. The readout of the supply load cell 94 may be shown to the user on the display screen 44. As the procedure proceeds, the readout of the supply load cell 94 may be updated in real time to alert the physician to how much fluid is left in the fluid supply source 34 and this amount may then be used to determine how much fluid has been infused into the patient. In some embodiments, the fluid management system 10 and/or the controller 48 may provide an amount of time remaining before a new fluid supply source 34 is needed based on the weight of the fluid supply source 34 and the rate at which the fluid supply source 34 is emptying (e.g., fluid flow rate). In some embodiments, the amount of fluid remaining in the fluid supply source 34 may be shown. An alert may be shown on the display screen 44 with an audible signal when, for example, 10% of the fluid is left in the fluid supply source 34. In some embodiments, the supply load cell 94 may connect to the display screen 44 via a wireless (e.g., Wi-Fi) signal. In some embodiments, the supply load cell 94 may be connected to the display screen 44 via a hard wire connection.

Similarly, the controller 48 may be configured to monitor the amount of fluid in the collection container 26 through weight using, for example, the collection load cell 25, a scale, or other suitable means. The collection load cell 25 may be used by the controller 48 to determine a weight of the collection container 26 to compare an initial amount of fluid in the collection container 26 to a current amount of fluid in the collection container 26. The readout of the collection load cell 25 may be shown to the user on the display screen 44. As the procedure proceeds, the readout of the collection load cell 25 may be updated in real time to alert the physician to how much fluid is in the collection container 26 and this amount may then be used to determine how much fluid has been collected from the patient and/or the collection drape 28. In some embodiments, the fluid management system 10 and/or the controller 48 may provide an amount of time remaining before a new collection container 26 is needed based on the weight of the collection container 26 and the rate at which the fluid supply source 34 is emptying (e.g., fluid flow rate). In some embodiments, the amount of fluid in the collection container 26 may be shown. An alert may be shown on the display screen 44 with an audible signal when, for example, 10% of an initial empty volume is left in the collection container 26. In some embodiments, the collection load cell 25 may connect to the display screen 44 via a wireless (e.g., Wi-Fi) signal. In some embodiments, the collection load cell 25 may be connected to the display screen 44 via a hard wire connection.

In some embodiments, fluid deficit calculation may continue uninterrupted when the collection container 26 is emptied or replaced. For example, if the collection container 26 is emptied or replaced during the procedure, the same procedure continues. As such, the fluid deficit being calculated by the controller 48 may also continue to maintain a total fluid deficit for the entire procedure. During the procedure, if the collection container 26 becomes full, it may be emptied and placed back into use, or the collection container 26 may be replaced by an empty collection container. In some embodiments, the controller 48 may be configured to retain the amount of fluid in the collection container 26, and the controller 48 may be configured to thereafter calculate the total fluid deficit by adding the amount of fluid in the collection container 26 to a second amount of fluid associated with the emptied collection container or the replacement collection container when the distal end 80 of the elongate shaft 76 is disposed within the patient.

In some embodiments, the controller 48 may be configured to calculate the fluid deficit using rotational speed of the inflow pump 50 in combination with a difference between a change in weight of the fluid supply source 34 and a change in weight of the collection container 26. For example, the rotational speed of the inflow pump 50 may define a known fluid flow rate (e.g., an expected amount of fluid infused into the patient and/or the treatment site), and the difference between the weight of fluid removed from the fluid supply source 34 and the weight of the fluid added to the collection container 26 may correspond to the fluid deficit (e.g., fluid lost). In some embodiments, the controller 48 may be configured to correlate the change in weight of the fluid supply source 34 with rotation speed of the inflow pump 50 and/or data from a flow sensor to determine if fluid is being lost at the fluid supply source 34, or at some location upstream of the treatment site and/or outside of the patient (e.g., a burst bag of fluid). In some embodiments, the controller 48 may be configured to calculate a first fluid deficit value using the rotational speed of the inflow pump 50 and a second fluid deficit valve using the difference between the change in weight of the fluid supply source 34 and the change in weight of the collection container 26. A displayed deficit value (e.g., on the display screen 44) may be based on a combination of the first fluid deficit value and the second fluid deficit value. For example, the first fluid deficit value may be compared to and/or correlated with the second fluid deficit value. In some embodiments, the controller 48 may be configured to display the displayed deficit value if a difference between the first fluid deficit value and the second fluid deficit value is within a predetermined range. In some embodiments, the controller 48 may be configured to display a notification if the difference between the first fluid deficit value and the second fluid deficit value is outside of the predetermined range.

In some embodiments, the fluid management system 10 may include a pressure sensor connected inline between the fluid supply source 34 and the medical device 20, wherein pressure within the supply line(s) 78 is determined based on the height of the fluid supply source 34. The amount of head pressure decreases as the fluid supply source 34 empties. When the pressure falls below a threshold set by the user, an alert may be shown on the display screen 44 and an audible signal may be emitted. In another exemplary embodiment, the controller 48 may be set to a specific fluid flow rate or fluid pressure based on the amount of time that has passed. The physician may enter an initial fluid volume of the fluid supply source 34 into the fluid management system 10 and/or the controller 48, which then calculates the amount of fluid already used and how much is left based on the known fluid flow rate or the known fluid pressure and the amount of time the fluid management system 10 has been in use. In some embodiments, a flow rate sensor may be connected inline between the fluid supply source 34 and the medical device 20. The flow rate sensor may be operably connected to the controller 48 and data from the flow rate sensor may be used by the controller 48 to change selected system parameters and/or may be used in the fluid deficit calculation(s).

The fluid management system 10 may utilize supply line(s) 78 to connect various components. In some embodiments, the supply line(s) 78 may formed from small diameter tubing less than or equal to ¹⁄₁₆ inches (1.5875 millimeters) in diameter. However, it will be understood that tubing size may vary based on the application. The supply line(s) 78 and/or the tubing may be disposable and provided sterile and ready to use. Different types of tubing may be used for various functions within the fluid management system 10. For example, one type of tubing may be used for fluid heating and fluid flow control to the medical device 20 while another type of tubing may be used for irrigation within the body and/or the treatment site.

Figure 5:
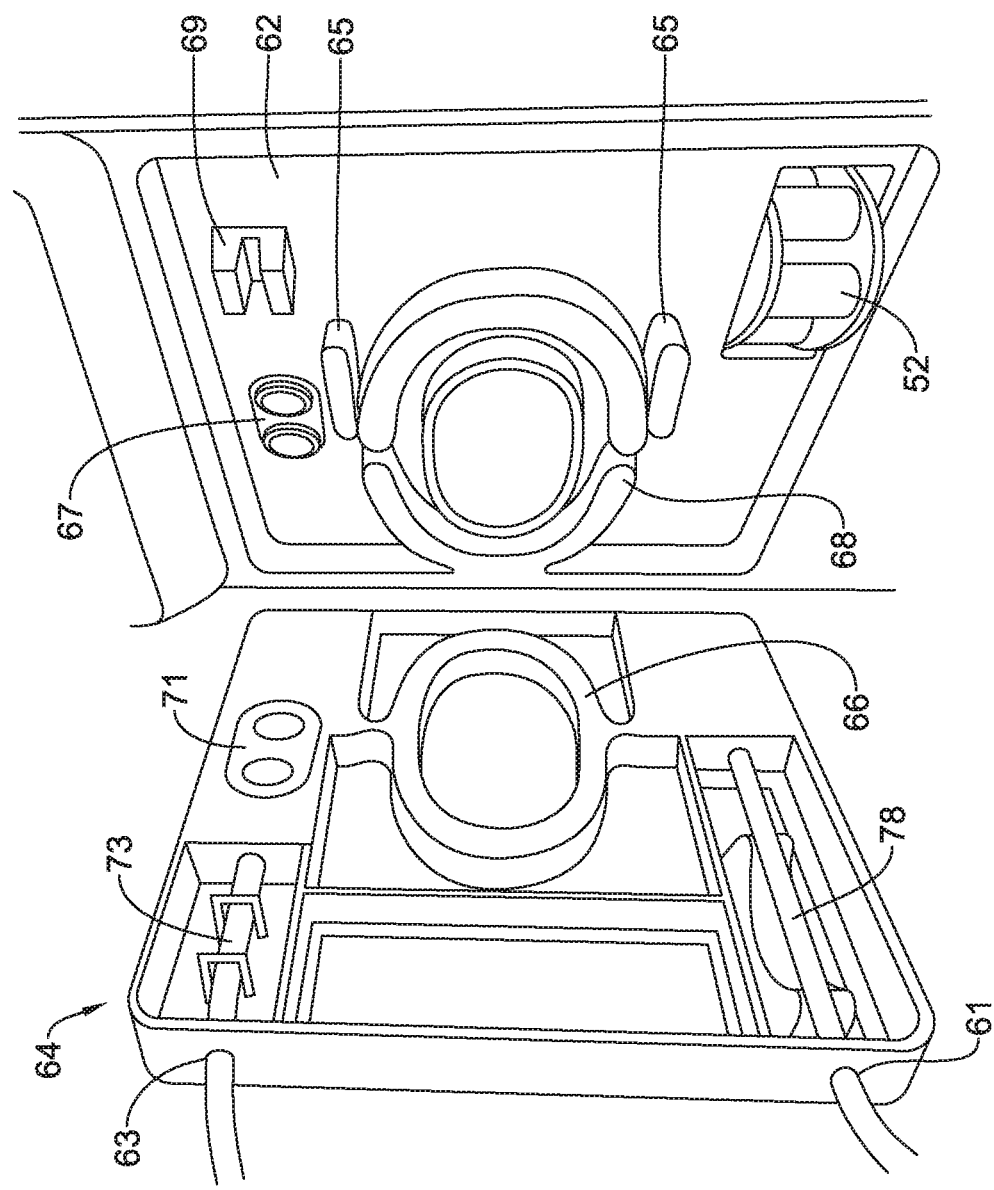
FIG. 5 is a partial perspective view illustrating selected aspects of a heater assembly and cassette of the system of FIG. 1.

In some embodiments, the fluid management system 10 may include a fluid warming system 60, as shown in FIG. 5, for heating fluid to be delivered to the patient. The fluid warming system 60 may include a heater 62 and a heater cassette 64. The heater cassette 64 may be configured to be a single use heater cassette 64 while the heater 62 may be reused for multiple procedures. For example, the heater cassette 64 may isolate fluid flow such that the heater 62 may be reused with minimal maintenance. The heater cassette 64 may be formed of, for example, polycarbonate or any high heat rated biocompatible plastic and is formed as a single unitary and/monolithic piece or a plurality of pieces permanently bonded to one another. In some embodiments, the heater cassette 64 may include a fluid inlet port 61 and a fluid outlet port 63 located at a lateral side of the heater cassette 64. The fluid inlet port 61 and the fluid outlet port 63 may each be configured to couple to the supply line(s) 78 of the fluid management system 10. For example, the fluid inlet port 61 may couple the fluid supply source 34 and the fluid warming system 60 (via the inflow pump 50) while the fluid outlet port 63 may couple the fluid warming system 60 with the medical device 20, each via the supply line(s) 78.

In some embodiments, the heater cassette 64 may include an internal flow path along a channel through which fluid may flow from the fluid inlet port 61 to the fluid outlet port 63. The heater cassette 64 may include one fluid path or multiple fluid paths. In some embodiments, the channel may pass through a susceptor 66 which may allow the fluid to be heated via induction heating. When the heater cassette 64 is coupled with the heater 62, the susceptor 66 may be configured to be positioned within an induction coil 68. Other fluid warming system configurations and methods may also be used, as desired. For example, the heater 62 may include one or more heat sources such as, for example a platen system or an inline coil in the supply line(s) 78 using electrical energy. Heating may be specifically designed and tailored to the flow rates required in the specific application of the fluid management system 10. Some illustrative fluid warming systems 60 are described in described in commonly assigned U.S. Patent Application Publication No. 2018/0361055, titled AUTOMATED FLUID MANAGEMENT SYSTEM, the entire disclosure of which is hereby incorporated by reference.

While not explicitly shown, the fluid warming system 60 may include a heater user interface separate from the touch screen interface 42. The heater user interface may simply be a display screen providing a digital display of the internal temperature of the heater 62. In another embodiment, the user interface may also include temperature adjustment buttons to increase or decrease the temperature of the heater 62. In this embodiment, the heater user interface and/or the display screen may indicate the current temperature of the heater 62 as well as the target temperature to be reached. It is noted that all information output from the fluid warming system 60 may be transmitted directly to the display screen 44 such that no heater user interface is necessary.

The fluid warming system 60 may include one or more sensors configured to monitor the fluid flowing therethrough. For example, temperature sensors 65 may be mounted in the fluid warming system 60 such that they detect the temperature of the fluid flowing through the heater cassette 64. The temperature sensors 65 may be located at or near the fluid inlet port 61 and/or the fluid outlet port 63. In some embodiments, the temperature sensors 65 may be mounted so that they detect the temperature of fluid flowing through the heater cassette 64 prior to the fluid entering the susceptor 66 and after fluid exits the susceptor 66. In some embodiments, additional sensors may be located at a medial portion of the susceptor 66 so that they detect a progression of temperature increase of the fluid in the heater cassette 64. The temperature sensors 65 may remotely send any information to the display screen 44 or they may send information to heater user interface and/or the display screen thereof, if so provided. In another embodiment, the temperature sensors 65 may be hardwired with the heater user interface (if provided) which is then able to remotely transmit desired information to the display screen 44. Alternatively, or additionally, the temperature sensors 65 may be hardwired to and/or with the controller 48.

The heater 62 may further include a pressure sensor 67 and/or a bubble sensor 69. The heater cassette 64 may include a corresponding pressure sensor interface 71 and bubble sensor interface 73 that allow the pressure sensor 67 and the bubble sensor 69, respectively, to monitor the fluid flowing through the heater cassette 64 when the heater cassette 64 is coupled with the fluid warming system 60. The pressure sensor 67 and/or the bubble sensor 69 may remotely send any information to the display screen 44 or they may send information to the heater user interface and/or the display screen thereof, if so provided. In another embodiment, the pressure sensor 67 and/or the bubble sensor 69 may be hardwired with the heater user interface (if provided) which is then able to remotely transmit desired information to the display screen 44. Alternatively, or additionally, the pressure sensor 67 and/or the bubble sensor 69 may be hardwired to and/or with the controller 48.

Figure 6:
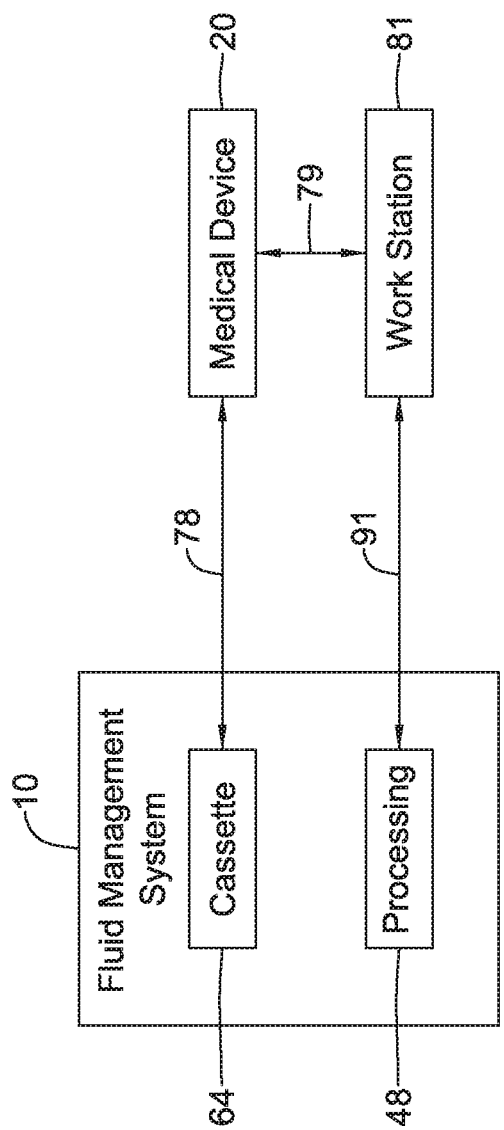
FIG. 6 is a schematic block diagram of the fluid management system and medical device of FIGS. 1 and 2.

FIG. 6 is a schematic block diagram illustrating the fluid management system 10 and the medical device 20. As described herein, there may be two primary interfaces between the fluid management system 10 and the medical device 20 including one or more mechanical connections (e.g., supply line(s) 78) fluidly coupling the medical device 20 to the heater cassette 64 and one or more wired or wireless communication connections 91 (e.g., an Ethernet cord, Wi-Fi, etc.) coupling the workstation 81 with the controller 48 of the fluid management system 10. The workstation 81 may transmit pressure data (e.g., obtained with the medical device 20) to the controller 48 of the fluid management system 10. The controller 48 of the fluid management system 10 may then use the pressure data from the medical device 20 to adjust fluid flow rates or fluid pressure when a user-specified or predetermined pressure limit is reached.

However, during a typical stone procedure, for example, the fluid management system 10 may be connected to multiple endoscopes, or other medical devices. Also, in a procedure where both the medical device 20 with the pressure sensor 74 and the fluid management system 10 are used, it may be that the controller 48 and the workstation 81 may be connected during the staging of the OR, and may remain connected throughout the procedure. This might mean if the medical device 20 is connected to the workstation 81, the workstation 81 may transmit pressure data to the controller 48 of the fluid management system 10 whether or not the medical device 20 is in use. Thus, the controller 48 of the fluid management system 10 may be configured to determine when it is safe to use the pressure data from the medical device 20 for regulating intracavity pressure. In some embodiments, this may be done by asking the user to select on the touch screen interface 42 the type of the medical device 20 being used. If the physician selects a device other than the medical device 20, the controller 48 of the fluid management system 10 may ignore the pressure data being sent from the medical device 20.

However, there can be cases where the physician incorrectly selects the medical device 20 when the physician is not actually using it or the physician may forget to tell the fluid management system 10 that the medical device 20 is no longer in use and a different scope or medical device is now in use. If the fluid management system 10 is unable to detect that a new scope or medical device is being used, the fluid management system 10 may incorrectly use the pressure data sent from the medical device 20 which is not in use (and therefore the pressure data is inaccurate relative to the intracavity pressure). As a result, this may essentially bypass the fluid management system 10 pressure limit control and allow the fluid management system 10 to drive or deliver potentially hazardous pressures. To prevent such hazards from occurring, it may be necessary for the fluid management system 10 to determine when it safe to use the pressure data transmitted from the medical device 20 via the workstation 81. Thus, it may be desirable to detect if a sensor-enabled medical device 20 is connected to the fluid management system 10 when the only connection between the medical device 20 and the fluid management system 10 may be a physical connection using, for example, a standard Luer connector.

When the medical device 20 is in use with the fluid management system 10, the medical device 20 may be exposed to several unique sources of pulsatile pressures that can be measured by the pressure sensor 74 at the distal tip of the medical device 20. These sources of pulsation can either be unique to the fluid management system 10 or to the patient. If one or more sources of pulsation can be distinguished, the fluid management system 10 can make the determination that the medical device 20 is in use and thus safe to limit fluid pressure based off the pressure data from the medical device 20.

One source of pulsatile pressure may be generated within the fluid management system 10. For example, the inflow pump 50 may create a unique fingerprint in its pulsatile flow that can be measured with a pressure sensor, such as the pressure sensor 74 of the medical device 20. The pulsatile pressure may be a function of the pump head rollers and the revolutions per minute (RPM) of the pump head. When the medical device 20 is connected to the fluid management system 10, this fingerprint can be measured by the medical device 20 and matched against the signature created by the inflow pump 50 of the fluid management system 10. When there is a match between the measured pulsatile pressure at the pressure sensor 74 of the medical device 20 and the known signature of the inflow pump 50 of the fluid management system 10, the fluid management system 10 can confirm the medical device 20 is in use and connected to the fluid management system 10.

In some embodiments, raw pressure data from the fluid management system 10 may be received from the pressure sensor 67 in the fluid warming system 60. In other embodiments, the raw pressure data may be retrieved from a database of expected pressures according to fluid flow rate. In the illustrative embodiment, the raw pressure data and pressure data from the medical device 20 is collected at a medium fluid flow rate of about 100 milliliters per minute (mL/min). However, it should be understood that the data processing steps described herein may be used for fluid flow rates less than 100 mL/min and greater than 100 mL/min. In order to compare the raw pressure data from the fluid management system 10 and the pressure data from the medical device 20, the raw pressure data and the pressure data from the medical device 20 may be filtered using math averaging. In some embodiments, the raw pressure data and the pressure data from the medical device 20 may be filtered with a low pass filter with a filter cutoff frequency. The filter cutoff frequency may be set based off of the pump flow rate. The raw pressure data and the pressure data from the medical device 20 may then be normalized. Next, a fast Fourier transform (FFT) algorithm may be performed on the filtered and normalized pressure data to extract a dominant tone created by the inflow pump 50. The FFT algorithm may convert the filtered and normalized pressure data from a time domain to a frequency domain. When the filtered and normalized pressure data is converted to the frequency domain, the dominant tone (e.g., the frequency having the greatest magnitude) of the fluid management system 10 and the dominant tone of medical device 20 can be identified. In some embodiments, the dominant tone of the fluid management system 10 and the dominant tone of the medical device 20 are similar or the same at about 2.3 Hertz (Hz). In the illustrated example, the fluid management system 10 may determine whether or not the dominant tones match. The dominant tones may be considered to match if they are equal, approximately equal, or within a predetermined range of one another. When the dominant tone of the fluid management system 10 and the dominant tone of the medical device 20 match, the fluid management system 10 can determine that the medical device 20 is in use and connected to the fluid management system 10 and the pressure data from the medical device 20 can be used to control fluid management system 10.

It is contemplated that data processing may occur at the controller 48, the workstation 81, or combinations thereof. In some embodiments, all of the raw pressure data and the pressure data from the medical device 20 may be processed and analyzed at a single processing device. In other embodiments, the raw pressure data and the pressure data from the medical device 20 may be processed at separate processing devices. For example, in some cases, the controller 48 may process (e.g., filter, normalized, and/or FFT) the raw pressure data obtained from the fluid management system 10 while the workstation 81 may process (e.g., filter, normalize, and/or FFT) the pressure data obtained from the medical device 20. In some cases, the processed pressure data from the medical device 20 may be transferred from the workstation 81 to the controller 48 for comparison. In other embodiments, the processed raw pressure data from the fluid management system 10 may be transferred from the controller 48 to the workstation 81 for analysis.

In some embodiments, for example at a higher fluid flow rate such as 400 mL/min, the dominant tone of the fluid management system 10 and the dominant tone of the medical device 20 may not be similar or the same. This is only an example, and is not intended to be limiting. In this example, the dominant tone of the fluid management system 10 may be about 9.5 Hz while the dominant tone of the medical device may be about 4 Hz. Accordingly, in this example, the fluid management system 10 may determine that the dominant tones do not match and thus the pressure data from the medical device 20 should not be used to control the fluid management system 10.

Another source of pulsatile pressure may be the patient's heartbeat. For example, pulsatile waves, which are synchronous with the heartbeat, may be transmitted to within renal pelvis. These pulsatile waves may create a unique pressure signature related to the cardiac rhythm that can be detected by the medical device 20. The fluid management system 10 may be configured to compare a characteristic extracted from the pressure signature of the heartbeat with a characteristic extracted from pressure data received from the pressure sensor 74 on the medical device 20. The characteristic may be a frequency, amplitude, dominant tone, etc. In one example, the fluid management system 10 may compare heartbeat data that has been filtered, normalized, and converted to the frequency domain to pressure data from the medical device 20 that has also been filtered, normalized, and converted to the frequency domain in a manner similar to that described above. It is contemplated that the heartbeat data may be obtained from a medical device other than the fluid management system 10 or the medical device 20. If the cardiac rhythm is detected in the pressure data collected by the medical device 20, the fluid management system 10 can make the determination that the medical device 20 is in use and thus the fluid management system 10 can use the pressure data obtained from the medical device 20 to control the fluid management system 10. If the cardiac rhythm cannot be detected in the pressure data collected by the medical device 20, the fluid management system 10 can make the determination that medical device 20 is not in use and the fluid management system 10 should not use the pressure data from the medical device 20 to control the fluid management system 10.

Another source of pulsatile pressure may be the ureteral renal pelvic activity of the patient. For example, the contraction and relaxation of the patient's ureter or renal pelvis may create a unique and measurable pressure wave. The periodic pressure changes from these contractions may be detected with the pressure sensor 74 in the medical device 20. The fluid management system 10 may be configured to compare a characteristic extracted from the pressure signature of the ureteral renal pelvic activity with a characteristic extracted from pressure data received from the pressure sensor 74 on the medical device 20. The characteristic may be a frequency, amplitude, dominant tone, etc. In some cases, the contractions may be detected with a sensor other than the medical device 20 or the fluid management system 10 for comparison to pressure data from the medical device 20. In other embodiments, the fluid management system 10 may be configured to compare an expected or preprogramed contraction pattern with the pressure data from the medical device 20. It is contemplated that the contraction data (if obtained during the medical procedure) may be filtered, normalized, and converted to the frequency domain prior to comparison with the pressure data from the medical device 20 which has also been filtered, normalized, and converted to the frequency domain in a manner similar to that described above. If the ureteral renal pelvic activity is detected in the pressure data from the medical device 20, the fluid management system 10 can make the determination that medical device 20 is in use and thus the fluid management system 10 can use the pressure data obtained from the medical device 20 to control the fluid management system 10. If the ureteral renal pelvic activity cannot be detected in the pressure data from the medical device 20, the fluid management system 10 can make the determination that medical device 20 is not in use and the fluid management system 10 should not use pressure data from the medical device 20 to control the fluid management system 10.

Yet another source of pulsatile pressure may be the patient's respiration. For example, the normal respiratory rhythm of the patient may create slow, time varying changes in intrarenal pressure. These slow changes in pressure may be measured by the pressure sensor 74 on the medical device 20 (when the medical device 20 is in use) and matched to the patient's respiratory rhythm. The fluid management system 10 may be configured to compare a characteristic extracted from the pressure signature of the respiratory rhythm with a characteristic extracted from the pressure data received from the pressure sensor 74 on the medical device 20. The characteristic may be a frequency, amplitude, dominant tone, etc. In an example, the fluid management system 10 may compare respiration data that has been filtered, normalized, and converted to the frequency domain to pressure data from the medical device 20 that has also been filtered, normalized, and converted to the frequency domain in a manner similar to that described above. It is contemplated that the respiration data may be obtained from a medical device other than the fluid management system 10 or the medical device 20. If the respiration rhythm is detected in the pressure data from the medical device 20, the fluid management system 10 can make the determination that the medical device 20 is in use and thus the fluid management system 10 can use the pressure data obtained from the medical device 20 to control the fluid management system 10. If the respiration rhythm cannot be detected in the pressure data from the medical device 20, the fluid management system 10 can make the determination that the medical device 20 is not in use and the fluid management system 10 should not use the pressure data from the medical device 20 to control the fluid management system 10.

In some embodiments, the fluid management system 10 may use pulsatile pressures to determine if the medical device 20 is in use within the body of the patient. To begin, the controller 48 of the fluid management system 10 may initiate a device verification process. It is contemplated that the controller 48 may be configured to perform the device verification process at predetermined intervals during the procedure (e.g., every minute, every five minutes, etc.). In other embodiments, the controller 48 may be configured to perform the device verification process each time the fluid management system 10 attempts to use the pressure data from the medical device 20 to control fluid flow from the fluid management system 10. Additionally, or alternatively, the device verification process may be manually initiated. For example, the physician may initiate the device verification process using the touch screen interface 42. The fluid management system 10 may then obtain the pressure data from the medical device 20. In some cases, the controller 48 may poll the workstation 81 for the raw pressure data over a predetermined time period, although this is not required. In some cases, the controller 48 may command the workstation 81 to obtain the pressure data from the medical device 20. The pressure data from the medical device 20 may then be filtered, normalized, and converted to the frequency domain. It is contemplated that the pressure data from the medical device 20 may be processed at the controller 48 or at the workstation 81, as desired.

The fluid management system 10 may also obtain pulsatile pressure data from the fluid management system 10 and/or the patient. Sources of pulsatile pressure data may include, but are not limited to, pressure pulses generated by the inflow pump 50, the patient's heartbeat, the patient's ureteral renal pelvic activity, the patient's respiratory rhythm, etc. It is contemplated that the fluid management system 10 may be configured to obtain the pulsatile pressure data over the same predetermined time period as (e.g., substantially simultaneously with) the pressure data from the medical device 20. However, in some instances, the fluid management system 10 may not obtain new data related to the pulsatile pressure data, but rather reference a predetermined baseline or expected data. The pressure data from the fluid management system 10 and/or the patient may then be filtered, normalized, and converted to the frequency domain. It is contemplated that the pressure data from the fluid management system 10 and/or the patient may be processed at the controller 48 or at the workstation 81, as desired.

The controller 48 or the workstation 81 may then compare the frequency domain data of the medical device 20 with the frequency domain data of the pulsatile pressure source. The controller 48 or the workstation 81 may then determine if the frequency domain data of the medical device 20 and the frequency domain data of the pulsatile pressure source match. If the frequency domain data of the medical device 20 and the frequency domain data of the pulsatile pressure source match, the fluid management system 10 determines the pressure data from the medical device 20 can be used to control the fluid flow from the fluid management system 10. If the frequency domain data of the medical device 20 and the frequency domain data of the pulsatile pressure source do not match, the fluid management system 10 determines the pressure data from the medical device 20 cannot or should not be used to control the fluid flow from the fluid management system 10.

Alternatively, or additionally, the data obtained from the temperature sensor 72 of the medical device 20 may be used to determine if the data from the pressure sensor 74 of the medical device 20 can be used to help control the fluid management system 10. To begin, the controller 48 may initiate a device verification process. It is contemplated that the controller 48 may be configured to perform the device verification process at predetermined intervals during the procedure (e.g., every minute, every five minutes, etc.). In other embodiments, the controller 48 may be configured to perform the device verification process each time the fluid management system 10 attempts to use the pressure data from the medical device 20 to control fluid flow from the fluid management system 10. Additionally, or alternatively, the device verification process may be manually initiated. For example, the physician may initiate the device verification process using the touch screen interface 42. The fluid management system 10 may then obtain temperature data from the medical device 20. In some cases, the controller 48 may poll the workstation 81 for raw data over a predetermined time period, although this is not required. In some cases, the controller 48 may command the workstation 81 to obtain the temperature data from the medical device 20.

The controller 48 or the workstation 81 may then determine if the temperature measurement from the medical device 20 is greater than room temperature (e.g., greater than about 20° C.-23° C.). In some cases, the controller 48 or the workstation 81 may then determine if the temperature measurement from the medical device 20 is around body temperature (e.g., about 37° C.). If the temperature measurement obtained from the temperature sensor 72 on the medical device 20 is greater than 20° C.-23° C. (e.g., room temperature) or about 37° C. (e.g., body temperature), the fluid management system 10 determines the pressure data from the medical device 20 can be used to control the fluid flow from the fluid management system 10. If the temperature measurement obtained from the temperature sensor 72 on the medical device 20 is about 20° C.-23° C. (e.g., room temperature) or less than 37° C. (e.g., body temperature), the fluid management system 10 determines the pressure data from the medical device 20 cannot or should not be used to control the fluid flow from the fluid management system 10. In some cases, the fluid management system 10 may be configured to determine the medical device 20 is in use any time the temperature measurement obtained at the temperature sensor 72 is greater than room temperature (e.g., greater than about 20° C.-23° C.). The fluid management system 10 may compare the temperature measurement obtained at the temperature sensor 72 to an ambient temperature measurement of the room (an accurately measured room temperature). In other cases, the fluid management system 10 may be configured such that any temperature measurement greater than 25° C., greater than 28° C., or greater than 30° C. obtained at the temperature sensor is above room temperature and thus the data from the medical device 20 is safe to use. In some embodiments, the temperature measurement obtained from the temperature sensor 72 on the medical device 20 may be compared to and/or correlated with a temperature setting of the fluid warming system 60. In some embodiments, if the fluid warming system 60 (e.g., the heater 62) is active, the temperature measurement obtained from the temperature sensor 72 may be ignored when determining whether the pressure data from the medical device 20 can be used to control the fluid flow from the fluid management system.

It is contemplated that the fluid management system 10 may be programmed with a first temperature range that may be considered about room temperature (e.g., 20° C.+/−5° C. or 23° C.+/−3° C.) or an accurate room temperature measurement may be inputted into the fluid management system 10 from an ambient temperature sensor provided with or otherwise communicating with the fluid management system 10, and a second temperature range that may be considered about body temperature (e.g., 37° C.+/−1° C. or 37° C.+/−2° C.). These are just examples. Other temperature ranges may be used as desired or appropriate for the environmental conditions. In some cases, the second temperature range may be selected such that it accounts for procedures in which the fluid management system 10 delivers fluid at temperatures greater than body temperature (e.g., for example when a laser is in use). In other cases, the second temperature range may be selected such that it accounts for procedures in which the fluid management system 10 delivers fluid at temperatures less than body temperature.

Alternatively, or additionally, the pressure data obtained from the pressure sensor 74 of the medical device 20 may be compared to atmospheric pressure to determine if the pressure data from the pressure sensor 74 of the medical device 20 can be used to help control the fluid management system 10. To begin, the controller 48 may initiate a device verification process. It is contemplated that the controller 48 may be configured to perform the device verification process at predetermined intervals during the procedure (e.g., every minute, every five minutes, etc.). In other embodiments, the controller 48 may be configured to perform the device verification process each time the fluid management system 10 attempts to use the pressure data from the medical device 20 to control fluid flow from the fluid management system 10. Additionally, or alternatively, the device verification process may be manually initiated. For example, the physician may initiate the device verification process using the touch screen interface 42. The fluid management system 10 may then obtain the pressure data from the medical device 20 while the fluid management system 10 is actively delivering fluid. In some cases, the controller 48 may poll the workstation 81 for raw pressure data over a predetermined time period, although this is not required. In some cases, the controller 48 may command the workstation 81 to obtain the pressure data from the medical device 20.

It is contemplated that if the medical device 20 is in the body while the fluid management system 10 is delivering fluid, the pressure data measured at the pressure sensor 74 of the medical device 20 will be greater than atmospheric pressure. The controller 48 or the workstation 81 may then determine if the pressure data from the medical device 20 is greater than atmospheric pressure. If the pressure data obtained from the pressure sensor 74 on the medical device 20 is above atmospheric pressure, the fluid management system 10 determines the pressure data from the medical device 20 can be used to control the fluid flow from the fluid management system 10. If the pressure data obtained from the pressure sensor 74 on the medical device 20 is at or about atmospheric pressure, the fluid management system 10 determines the pressure data from the medical device 20 cannot or should not be used to control the fluid flow from the fluid management system 10. It is contemplated that an average pressure measurement and/or a root mean square (RMS) DC pressure from the pressure sensor 74 may be used to compare against atmospheric pressure.

Alternatively, or additionally, data obtained from the Fiber Bragg grating optical fiber 75 at the distal end 80 of the medical device 20 may be used to determine if the data from the pressure sensor 74 of the elongate shaft 76 can be used to help control the fluid management system 10. For example, the Fiber Bragg grating optical fiber 75 may detect stress along the elongate shaft 76 of the medical device 20 that occurs during normal use of the medical device 20. To begin, the controller 48 may initiate a device verification process. It is contemplated that the controller 48 may be configured to perform the device verification process at predetermined intervals during the procedure (e.g., every minute, every five minutes, etc.). In other embodiments, the controller 48 may be configured to perform the device verification process each time the fluid management system 10 attempts to use the pressure data from the medical device 20 to control fluid flow from the fluid management system 10. Additionally, or alternatively, the device verification process may be manually initiated. For example, the physician may initiate the device verification process using the touch screen interface 42. The fluid management system 10 may then obtain stress data from the Fiber Bragg grating optical fiber 75, or other stress measurement device, at the distal end 80 of the elongate shaft 76 of the medical device 20. In some cases, the controller 48 may poll the workstation 81 for raw data over a predetermined time period, although this is not required. In some cases, the controller 48 may command the workstation 81 to obtain the stress data from the medical device 20.

It is contemplated that if the medical device 20 is in the body, the Fiber Bragg grating optical fiber 75 may detect stresses in the elongate shaft 76 caused by normal use of the medical device 20. The controller 48 or the workstation 81 may then determine if the stress data from the medical device 20 are detected. If stresses are detected, the fluid management system 10 determines the pressure data from the medical device 20 can be used to control the fluid flow from the fluid management system 10. If stresses are not detected, the fluid management system 10 determines the pressure data from the medical device 20 cannot or should not be used to control the fluid flow from the fluid management system 10. In some cases, the stress data may be compared to a predetermined threshold. For example, if the stresses are above a certain level the medical device 20 is in use while if the stresses are at or below the certain level, the medical device 20 is not in use.

Alternatively, or additionally, the location of the distal end 80 of the elongate shaft 76 may be tracked to determine if the medical device 20 is in use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be coupled to a control unit which may include among other features, a processor, a memory, a display, and an input means.

A position sensor (e.g., the electromagnetic sensor 93, etc.) or other antenna, may be incorporated into the distal end 80 of the elongate shaft 76 of the medical device 20. The position sensor may be configured for use in sensing a location of the position sensor in the magnetic field of the mapping and navigation system. The position sensor may be electronically coupled to the workstation 81. When the position sensor is in the magnetic field, the location of the position sensor can be mathematically determined relative to the electromagnetic field source (e.g., the operating table and/or the electromagnetic generator). The workstation 81 and the control unit may communicate to determine the position of the position sensor relative to the patient. When the position sensor is disposed within the patient, the fluid management system 10 determines the pressure data from the medical device 20 can be used to control the fluid flow from the fluid management system 10. When the electromagnetic sensor is not disposed within the patient, the fluid management system 10 determines the pressure data from the medical device 20 cannot or should not be used to control the fluid flow from the fluid management system 10.

It may be desirable to reduce the likelihood of falsely determining the medical device 20 is in the body when in actuality, the medical device 20 is not in the body. For example, if the medical device 20 is not in the body but a user touches the temperature sensor 72, the medical device 20 may report to the fluid management system 10 the temperature is near body temperature, thus creating a false detection. It is contemplated that it may be desirable to use more than one sensor or device verification process, as described herein, to determine if the medical device 20 is in the body. It is contemplated that the results from the two or more device verification processes may be obtained substantially simultaneously (e.g., in parallel) or sequentially (e.g., one after the other), as desired. The fluid management system 10 may use any number of device verification processes and in any combination, as desired.

The controller 48 may compare the results to determine the number of device verification processes that confirm the medical device 20 is in use with the number of device verification processes that indicate the medical device 20 is not in use. The controller 48 may then determine if a majority of the device verification processes confirm the medical device 20 is in use. If the majority of the device verification processes confirm the medical device 20 is in use, the fluid management system 10 determines the pressure data from the medical device 20 can be used to control the fluid flow from the fluid management system 10. If the majority of the device verification processes do not or fail to confirm the medical device 20 is in use, the fluid management system 10 determines the pressure data from the medical device 20 cannot or should not be used to control the fluid flow from the fluid management system 10.

Alternatively, or additionally to determining if the majority of the device verification processes confirm or do not confirm the medical device 20 is in use, when at least one device verification process returns a result that is different from one or more additional device verification processes, the controller 48 may be configured to apply a weighted average to the results. For example, if one device verification process is deemed to be more accurate than other device verification processes, the more accurate device verification process may be weighted more heavily during the comparison step than the other device verification processes. Other techniques for comparing and analyzing the results from the device verification processes may be used as desired.

Figure 7:
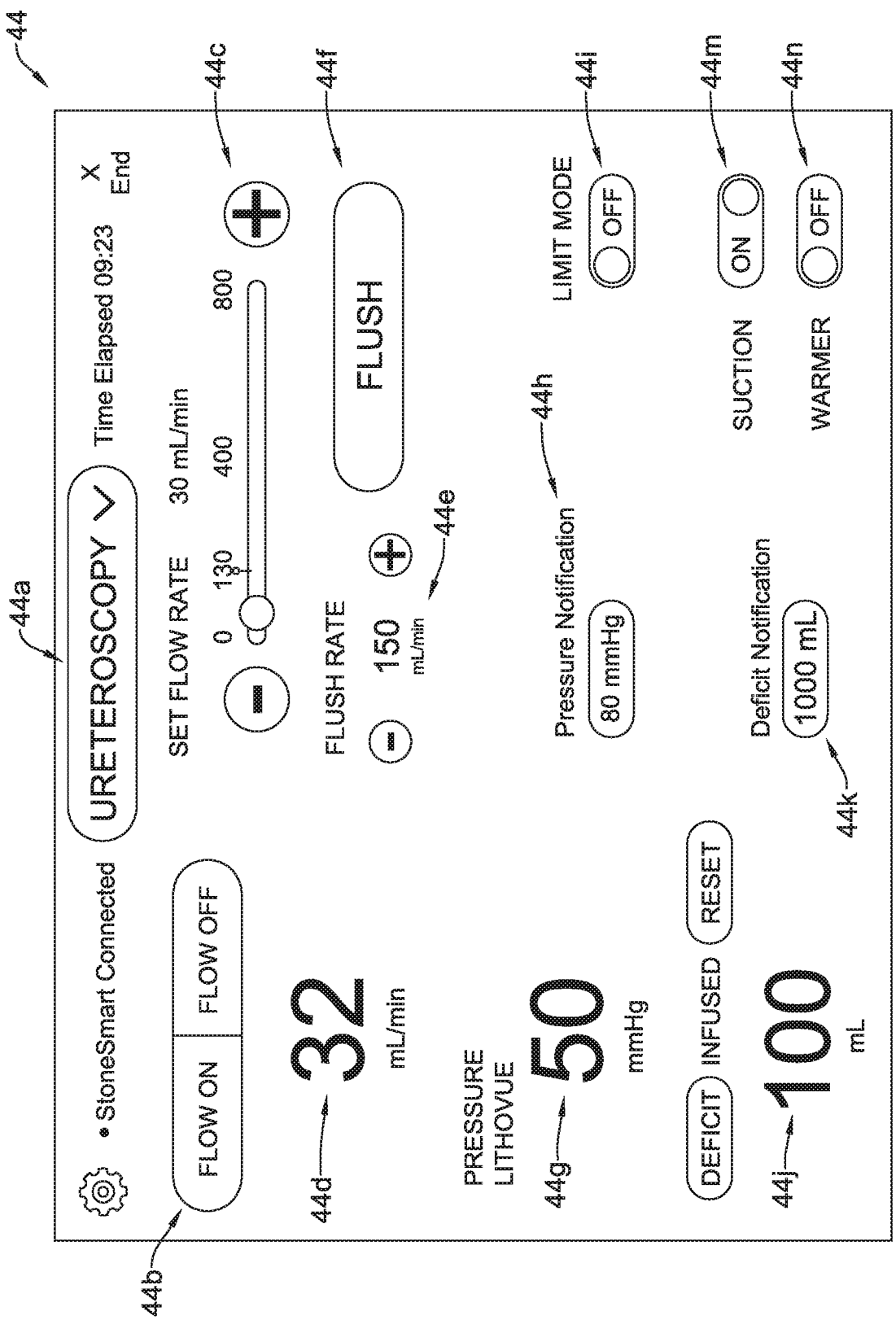
FIG. 7 illustrates an example display screen.

FIG. 7 illustrates an example display screen 44 of the controller 48. In some embodiments, the display screen 44 may include a selectable menu 44*a* for procedure and/or medical device type. In some embodiments, the display screen 44 may include a selectable switch 44*b* for turning fluid flow on or off. In some embodiments, the display screen 44 may include a flow rate selector 44*c* that may be defined by the user. In some embodiments, the display screen 44 may include a flow rate indicator 44d for showing the current/actual fluid flow rate. In some embodiments, the display screen 44 may include a flush rate selector 44e that may be defined by the user. In some embodiments, the display screen 44 may include a flush button 44f for initiating a burst of fluid flow manually. In some embodiments, the display screen 44 may include an intracavity pressure display 44g showing the intracavity pressure received from the medical device 20. In some embodiments, the display screen 44 may include a pressure notification setting 44h that may be defined by the user. In some embodiments, the display screen 44 may include a pressure limit mode switch 44i for activating automatic intracavity pressure control by the controller 48. In some embodiments, the display screen 44 may include a fluid amount display 44j that may be user-selectable to show the current amount of the fluid deficit or the current amount of fluid that has been infused during the procedure. In some embodiments, the display screen 44 may include a fluid deficit notification setting 44k that may be defined by the user. In some embodiments, the display screen 44 may include a vacuum pump activation switch 44m for turning the fluid collection system on or off. In some embodiments, the display screen 44 may include a fluid warmer activation switch 44n for turning the fluid warming system 60 on or off.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the fluid management system, the medical device, the elongate shaft, the inflow pump, the fluid warming system, the controller, the supply line(s), the load cells, the handle, the workstation, the display screen(s), the fluid supply source(s), the collection container(s), and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MM) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethylketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A fluid management and medical device system, comprising:
   a medical device comprising:
      an elongate shaft configured to access a treatment site within a patient;
      one or more sensors proximate a distal end of the elongate shaft; and
      a handle coupled to a proximal end of the elongate shaft; and
   a fluid management system comprising:
      an inflow pump configured to pump fluid from a fluid supply source to the treatment site; and
      a controller configured to calculate a fluid deficit when the distal end of the elongate shaft is disposed within the patient;
   wherein the controller is configured to automatically pause fluid deficit calculation when the distal end of the elongate shaft is removed from the patient.

2. The fluid management and medical device system of claim 1, wherein the controller is configured to resume the fluid deficit calculation when signals from the one or more sensors indicate the distal end of the elongate shaft is reinserted into the patient.

3. The fluid management and medical device system of claim 1, wherein the controller is configured to control the inflow pump to maintain a target fluid flow rate or a target fluid pressure based on a set of system operating parameters.

4. The fluid management and medical device system of claim 1, wherein the controller is configured to automatically reset the fluid deficit to zero after priming of the fluid management system.

5. The fluid management and medical device system of claim 4, wherein the controller is configured to automatically begin the fluid deficit calculation when signals from the one or more sensors indicate the distal end of the elongate shaft is inserted within the patient.

6. The fluid management and medical device system of claim 1, wherein the one or more sensors includes a temperature sensor.

7. The fluid management and medical device system of claim 1, wherein the one or more sensors includes a pressure sensor.

8. The fluid management and medical device system of claim 1, wherein the one or more sensors includes a temperature sensor and a pressure sensor.

9. The fluid management and medical device system of claim 1, wherein the fluid deficit calculation continues uninterrupted when the fluid supply source is replenished.

10. A fluid management and medical device system, comprising:
    a medical device comprising:
       an elongate shaft configured to access a treatment site within a patient;
       one or more sensors proximate a distal end of the elongate shaft; and
       a handle coupled to a proximal end of the elongate shaft; and
    a fluid management system comprising:
       a fluid supply source operatively coupled to a supply load cell and in fluid communication with the elongate shaft;
       a collection container operatively coupled to a collection load cell and in fluid communication with a collection drape;
       an inflow pump configured to pump fluid from the fluid supply source to the treatment site; and
       a controller configured to control the inflow pump to maintain a desired fluid pressure at the treatment site or a desired fluid flow rate based on a set of system operating parameters;
    wherein the controller is in electronic communication with the supply load cell and the collection load cell;
    wherein the controller is configured to calculate a fluid deficit using rotational speed of the inflow pump in combination with a difference between a change in weight of the fluid supply source and a change in weight of the collection container.

11. The fluid management and medical device system of claim 10, wherein the controller is configured to calculate the fluid deficit only when the distal end of the elongate shaft is disposed within the patient.

12. The fluid management and medical device system of claim 11, wherein the controller is configured to automatically pause fluid deficit calculation when the distal end of the elongate shaft is removed from the patient.

13. The fluid management and medical device system of claim 10, wherein the controller is configured to calculate a first fluid deficit value using a flow rate of the fluid and a second fluid deficit value using the difference between the change in weight of the fluid supply source and the change in weight of the collection container;
   wherein a displayable deficit value is based on a combination of the first fluid deficit value and the second fluid deficit value.

14. The fluid management and medical device system of claim 13, wherein the flow rate of the fluid is determined by the controller using the rotational speed of the inflow pump.

15. The fluid management and medical device system of claim 13, wherein the flow rate of the fluid is determined by the controller using data from a flow sensor disposed between the fluid supply source and the treatment site.

16. The fluid management and medical device system of claim 13, wherein the controller is configured to display the displayable deficit value if a difference between the first fluid deficit value and the second fluid deficit value is within a predetermined range;
   wherein the controller is configured to display a notification if the difference between the first fluid deficit value and the second fluid deficit value is outside of the predetermined range.

* * * * *